(12) United States Patent
Gonzales

(10) Patent No.: US 6,230,332 B1
(45) Date of Patent: May 15, 2001

(54) HEAD MANIPULATING DEVICE

(76) Inventor: Charlie C. Gonzales, 2045 W. Sindle Pl., Tucson, AZ (US) 85746

( * ) Notice: Subject to any disclaimer, the term of this patent is extended or adjusted under 35 U.S.C. 154(b) by 0 days.

(21) Appl. No.: 09/573,973

(22) Filed: May 19, 2000

(51) Int. Cl.[7] ....................................................... A42B 1/24
(52) U.S. Cl. ................................ 2/209.13; 2/209.3; 2/171
(58) Field of Search ........................... 2/209.13, 171.2, 2/195.1, 181, 174, 195.5, 195.6, 175.1, 175.4, 175.7, 171, 209.14, 209.3, DIG. 11; 482/10, 11, 124; 602/17, 18, 32, 36; 601/39

(56) References Cited

U.S. PATENT DOCUMENTS

| D. 270,014 | * | 8/1983 | Lutzker | D2/230 |
|---|---|---|---|---|
| 3,437,339 | * | 4/1969 | Starck | 2/209.13 |
| 4,179,753 | * | 12/1979 | Aronberg et al. | 2/209.13 |
| 4,739,526 | | 4/1988 | Hollick . | |
| 4,832,333 | * | 5/1989 | Lockett | 482/10 |
| 4,839,926 | * | 6/1989 | Choi | 2/199 |
| 5,003,639 | * | 4/1991 | White | 2/209.13 |
| 5,046,195 | | 9/1991 | Koritan . | |
| 5,203,694 | * | 4/1993 | Klein | 2/171.2 |
| 5,628,070 | | 5/1997 | Kefelian . | |
| 5,675,840 | | 10/1997 | Clavelle . | |
| 5,826,272 | * | 10/1998 | Hong | 2/209.13 |
| 6,000,063 | * | 12/1999 | Sullivan | 2/209.13 |
| 6,000,066 | * | 12/1999 | Williams | 482/10 |
| 6,009,555 | * | 1/2000 | Siprut | 2/209.3 |
| 6,029,272 | * | 2/2000 | Bazin | 2/209.13 |
| 6,061,837 | * | 5/2000 | Oh | 2/195.1 |

* cited by examiner

Primary Examiner—Amy B. Vanatta

(57) ABSTRACT

A head manipulating device for assisting movement of a user's head following an injury. The head manipulating device includes a first band member having ends and being adapted to extend about a back and sides of a user's head; and also includes a second band member having ends and being adapted to extend about a front and the sides of the user's head and being removably and adjustably fastened to the first band member; and further includes a visor member being securely attached to the second band member; and also includes a head lift member being removably and pivotally connected to the first band member and being extended about the front of the user's head; and further includes fastening members for fastening the first and second band members together.

10 Claims, 2 Drawing Sheets

HEAD MANIPULATING DEVICE

BACKGROUND OF THE INVENTION

1. Field of the Invention

The present invention relates to a head lift device and more particularly pertains to a new head manipulating device for assisting movement of a user's head following an injury.

2. Description of the Prior Art

The use of a head lift device is known in the prior art. More specifically, a head lift device heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,832,333; 4,739,526; 5,046,195; 5,628,070; 5,675,840; and U.S. Pat. No. Des. 270,014.

While these devices fulfill their respective, particular objectives and requirements, the aforementioned patents do not disclose a new head manipulating device. The inventive device includes a first band member having ends and being adapted to extend about a back and sides of a user's head; and also includes a second band member having ends and being adapted to extend about a front and the sides of the user's head and being removably and adjustably fastened to the first band member; and further includes a visor member being securely attached to the second band member; and also includes a head lift member being removably and pivotally connected to the first band member and being extended about the front of the user's head; and further includes fastening members for fastening the first and second band members together.

In these respects, the head manipulating device according to the present invention substantially departs from the conventional concepts and designs of the prior art, and in so doing provides an apparatus primarily developed for the purpose of assisting movement of a user's head following an injury.

SUMMARY OF THE INVENTION

In view of the foregoing disadvantages inherent in the known types of head lift device now present in the prior art, the present invention provides a new head manipulating device construction wherein the same can be utilized for assisting movement of a user's head following an injury.

The general purpose of the present invention, which will be described subsequently in greater detail, is to provide a new head manipulating device which has many of the advantages of the head lift device mentioned heretofore and many novel features that result in a new head manipulating device which is not anticipated, rendered obvious, suggested, or even implied by any of the prior art head lift device, either alone or in any combination thereof.

To attain this, the present invention generally comprises a first band member having ends and being adapted to extend about a back and sides of a user's head; and also includes a second band member having ends and being adapted to extend about a front and the sides of the user's head and being removably and adjustably fastened to the first band member; and further includes a visor member being securely attached to the second band member; and also includes a head lift member being removably and pivotally connected to the first band member and being extended about the front of the user's head; and further includes fastening members for fastening the first and second band members together.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new head manipulating device which has many of the advantages of the head lift device mentioned heretofore and many novel features that result in a new head manipulating device which is not anticipated, rendered obvious, suggested, or even implied by any of the prior art head lift device, either alone or in any combination thereof.

It is another object of the present invention to provide a new head manipulating device which may be easily and efficiently manufactured and marketed.

It is a further object of the present invention to provide a new head manipulating device which is of a durable and reliable construction.

An even further object of the present invention is to provide a new head manipulating device which is susceptible of a low cost of manufacture with regard to both materials and labor, and which accordingly is then susceptible of low prices of sale to the consuming public, thereby making such head manipulating device economically available to the buying public.

Still yet another object of the present invention is to provide a new head manipulating device which provides in the apparatuses and methods of the prior art some of the advantages thereof, while simultaneously overcoming some of the disadvantages normally associated therewith.

Still another object of the present invention is to provide a new head manipulating device for assisting movement of a user's head following an injury.

Yet another object of the present invention is to provide a new head manipulating device which includes a first band member having ends and being adapted to extend about a back and sides of a user's head; and also includes a second band member having ends and being adapted to extend about a front and the sides of the user's head and being removably and adjustably fastened to the first band member; and further includes a visor member being securely attached to the second band member; and also includes a head lift member being removably and pivotally connected to the first band member and being extended about the front of the user's head; and further includes fastening members for fastening the first and second band members together.

Still yet another object of the present invention is to provide a new head manipulating device that supports the user's head while lifting or lowering the user's head.

Even still another object of the present invention is to provide a new head manipulating device that substantially reduces further injury to the person's head or neck while manipulating the user's head.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
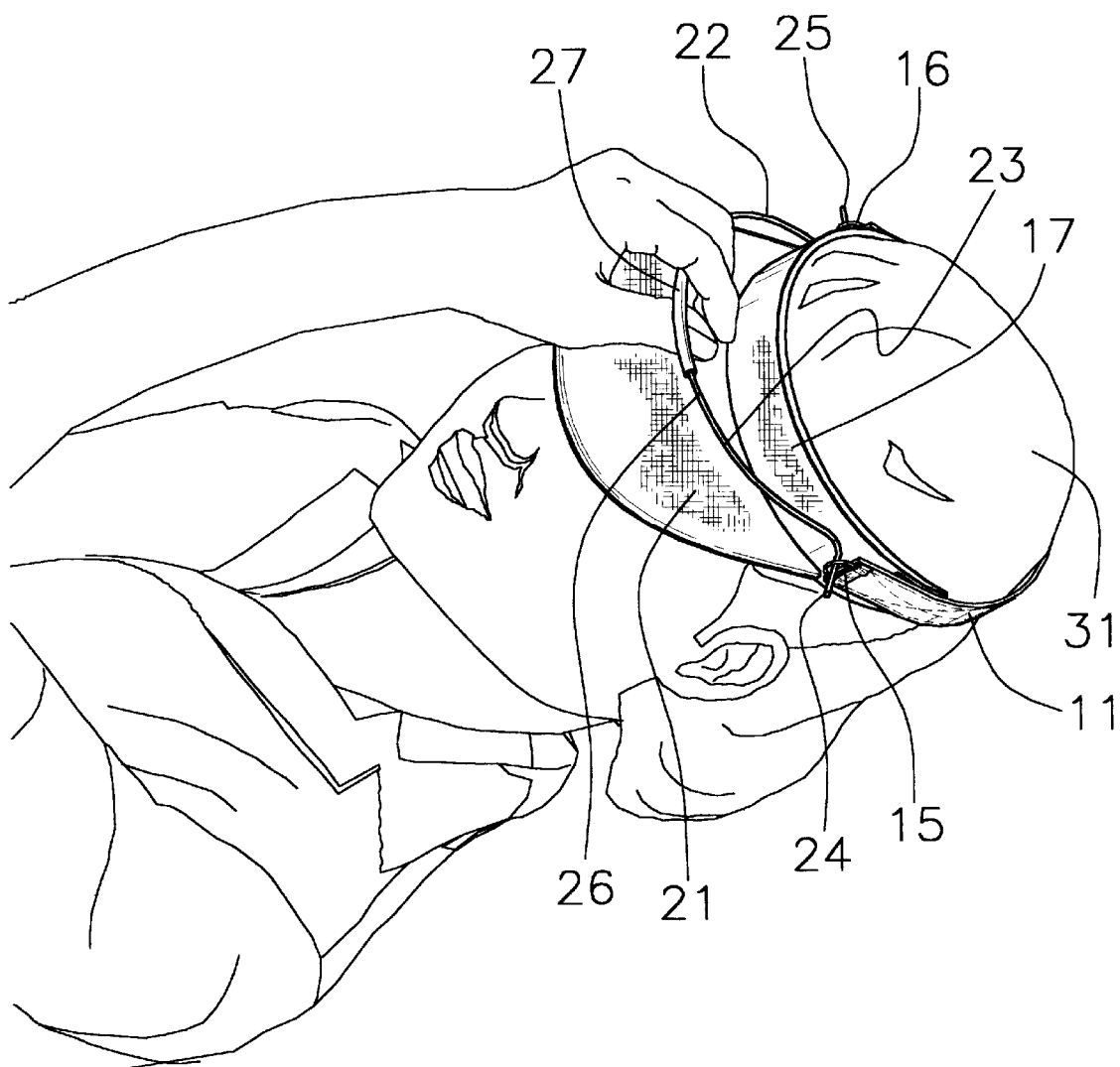
FIG. 1 is a perspective view of a new head manipulating device according to the present invention shown in use.
Figure 2:
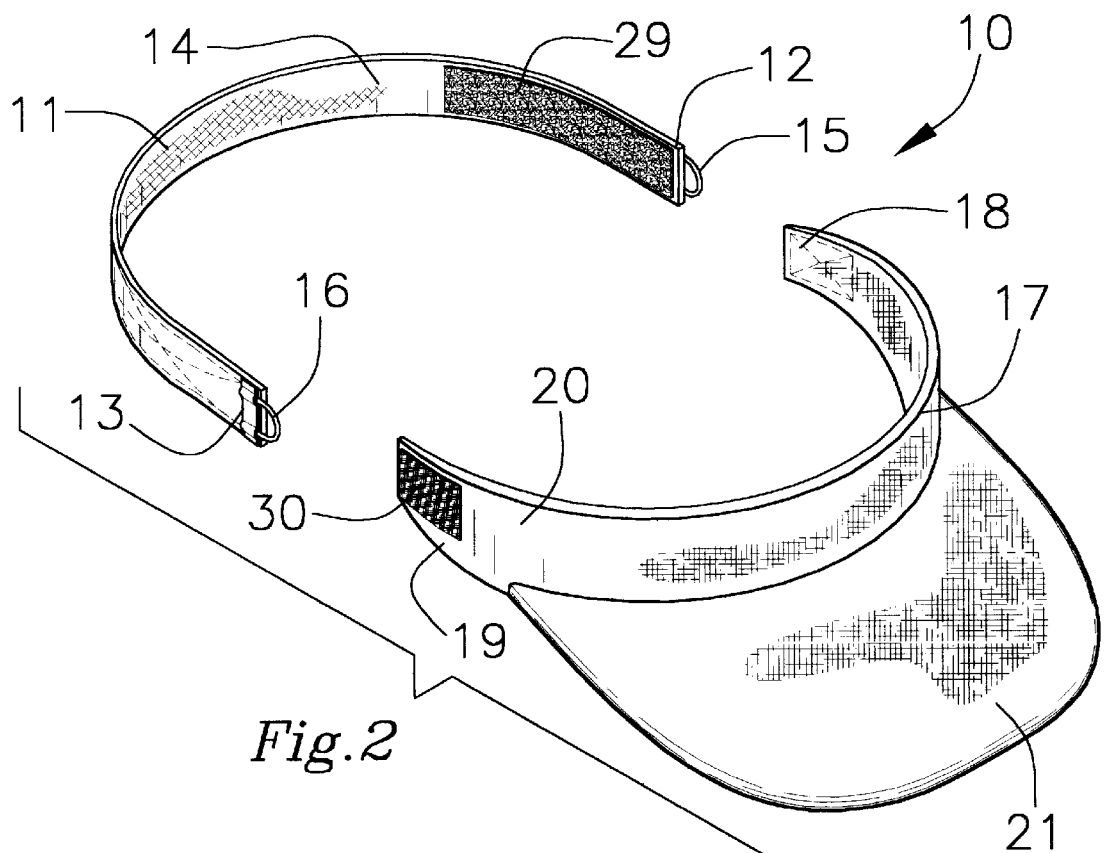
FIG. 2 is an exploded perspective view of the first and second band members of the present invention.
Figure 3:
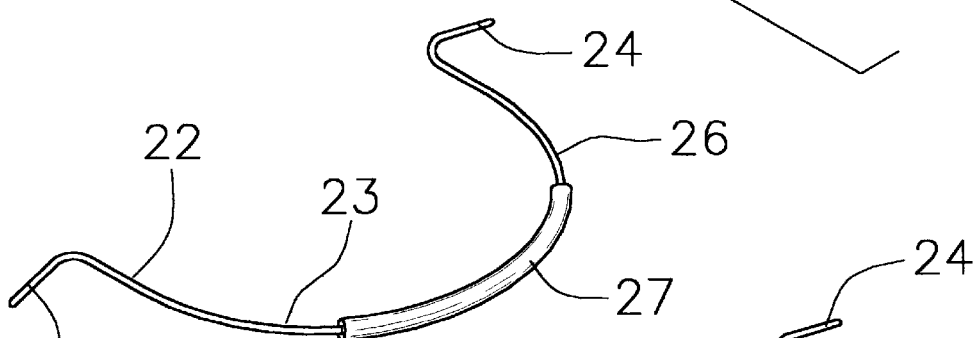
FIG. 3 is a perspective view of a first embodiment of the head lift member of the present invention.
Figure 4:
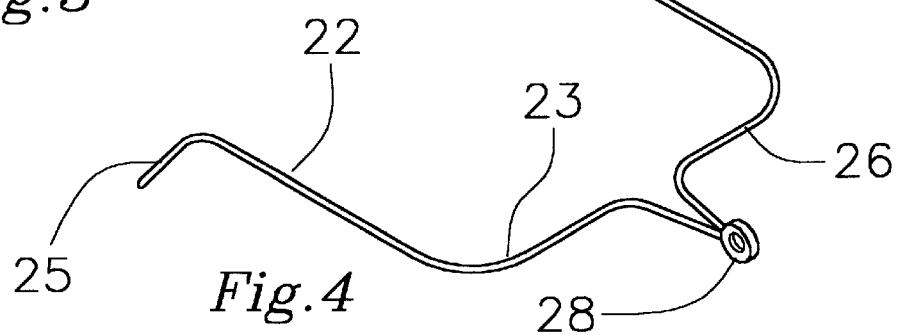
FIG. 4 is a perspective view of a second embodiment of the head lift member of the present invention.

With reference now to the drawings, and in particular to FIGS. 1 through 4 thereof, a new head manipulating device embodying the principles and concepts of the present invention and generally designated by the reference numeral 10 will be described.

As best illustrated in FIGS. 1 through 4, the head manipulating device 10 generally comprises a first band member 11 having ends 12,13 and being adapted to extend about a back and sides of a user's head 31; and also comprises a second band member 17 having ends 18,19 and being adapted to extend about a front and the sides of the user's head 31 and being removably and adjustably fastened to the first band member 11. A visor member 21 is securely and conventionally attached and sewn to the second band member 17 and extends therefrom.

A head lift member 22 is removably and pivotally connected to the first band member 11 and is extended about the front of the user's head 31. The head lift member 22 including an arcuate wire member 23 having curved ends 24,25 which are removably connected to the ends 12,13 of the first band member 11. The first band member 11 includes a pair of eyelets 15,16 each of which is securely and conventionally attached and sewn to a respective end 12,13 of the first band member 11 and each of which is adapted to receive a respective curved end 24,25 of the wire member 23.

Fastening members 29,30 for fastening the first and second band members 11,17 together include first fastening members 29 being securely and conventionally attached and sewn near the ends 12,13 and along portions of an inner side 14 of the first band member 11, and also includes second fastening members 30 being securely attached near the ends 18,19 and along portions of an outer side 20 of the second band member 17. Each of the first fastening members 29 are fastenable to a respective second fastening member 30 with the first and second band members 11,17 being adjustably fitted about the user's head 31. The fastening members 29,30 are essentially strips of hook and loop fasteners.

As a first embodiment, the head lift member 22 further includes a handle grip member 27 securely and conventionally disposed about a main portion 26 of the wire member 23 for a person to grasp to effectively manipulate the user's head 31.

As a second embodiment, the head lift member 22 further includes an eyelet member 28 securely and conventionally attached a main portion 26 of the wire member 23 intermediate of the curved ends 24,25 thereof and being adapted to connect to a cable for lifting and manipulating the user's head 31.

In use, the user would place the connected first and second band members 11,17 about one's head 31 with the visor member 21 being disposed to the front of the user's head 31, and would insert the curved ends 24,25 of the head lift member 22 through the respective eyelets 15,16 at the ends 12,13 of the first band member 11, and would use the head lift member 22 to lift and manipulate one's head 31 especially if the user had suffered some sort of head or neck injury.

As to a further discussion of the manner of usage and peration of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A head manipulating device comprising:
    a first band member having ends and being adapted to extend about a back and sides of a user's head;
    a second band member having ends and being adapted to extend about a front and the sides of the user's head and being adjustably and removably fastened to said first band member;

a visor member being securely attached to said second band member;

a head lift member being removably and pivotally connected to said first band member and being extended about the front of the user's head; and fastening members for fastening said first and second band members together.

2. A head manipulating device as described in claim 1, wherein said head lift member includes an arcuate wire member having curved ends which are removably connected to said ends of said first band member.

3. A head manipulating device as described in claim 2, wherein said first band member includes a pair of eyelets each of which is securely attached to a respective said end of said first band member and each of which is adapted to receive a respective said curved end of said wire member.

4. A head manipulating device as described in claim 3, wherein said fastening members include first fastening members being securely attached near said ends and along portions of an inner side of said first band member, and also include second fastening members being securely attached near said ends and along portions of an outer side of said second band member, each of said first fastening members being fastenable to a respective said second fastening member, said first and second band members being adjustably fitted about the user's head.

5. A head manipulating device as described in claim 4, wherein said fastening members are strips of hook and loop fasteners.

6. A head manipulating device as described in claim 5, wherein said head lift member further includes a handle grip member securely disposed about a main portion of said wire member for grasping to effectively manipulate the user's head.

7. A head manipulating device as described in claim 5, wherein said head lift member further includes an eyelet member securely attached a main portion of said wire member intermediate of said curved ends thereof and being adapted to connect to a cable for lifting and manipulating the user's head.

8. A head manipulating device comprising:

a first band member having ends and being adapted to extend about a back and sides of a user's head;

a second band member having ends and being adapted to extend about a front and the sides of the user's head and being adjustably and removably fastened to said first band member;

a visor member being securely attached to said second band member;

a head lift member being removably and pivotally connected to said first band member and being extended about the front of the user's head, said head lift member including an arcuate wire member having curved ends which are removably connected to said ends of said first band member, said first band member including a pair of eyelets each of which is securely attached to a respective said end of said first band member and each of which is adapted to receive a respective said curved end of said wire member; and fastening members for fastening said first and second band members together, said fastening members including first fastening members being securely attached near said ends and along portions of an inner side of said first band member, and also including second fastening members being securely attached near said ends and along portions of an outer side of said second band member, each of said first fastening members being fastenable to a respective said second fastening member, said first and second band members being adjustably fitted about the user's head, said fastening members being essentially strips of hook and loop fasteners.

9. A head manipulating device as described in claim 8, wherein said head lift member further includes a handle grip member securely disposed about a main portion of said wire member for grasping to effectively manipulate the user's head.

10. A head manipulating device as described in claim 8, wherein said head lift member further includes an eyelet member securely attached a main portion of said wire member intermediate of said curved ends thereof and being adapted to connect to a cable for lifting and manipulating the user's head.

* * * * *